United States Patent

Chau et al.

[19]

[11] Patent Number: 5,859,698
[45] Date of Patent: Jan. 12, 1999

[54] METHOD AND APPARATUS FOR MACRO DEFECT DETECTION USING SCATTERED LIGHT

[75] Inventors: Henry K. Chau, San Francisco; Arun A. Aiyer, Fremont, both of Calif.

[73] Assignee: Nikon Corporation, Tokyo, Japan

[21] Appl. No.: 852,849

[22] Filed: May 7, 1997

[51] Int. Cl.[6] .............................. G01N 21/00; C06K 9/00
[52] U.S. Cl. ........................ 356/237; 382/149; 382/218
[58] Field of Search ................................. 356/237, 239, 356/394, 371; 382/149, 218, 259, 108, 281, 141; 348/125, 87

[56] References Cited

U.S. PATENT DOCUMENTS

| | | | |
|---|---|---|---|
| 5,129,009 | 7/1992 | Lebeau | 382/8 |
| 5,179,419 | 1/1993 | Palmquist et al. | 356/237 |
| 5,298,963 | 3/1994 | Moriya et al. | 356/237 |
| 5,365,596 | 11/1994 | Dante et al. | 356/237 |
| 5,371,690 | 12/1994 | Engel et al. | 364/570 |
| 5,434,629 | 7/1995 | Pearson et al. | 348/721 |
| 5,544,256 | 8/1996 | Brecher et al. | 382/149 |
| 5,548,326 | 8/1996 | Michael | 348/87 |

*Primary Examiner*—Hoa Q. Pham
*Attorney, Agent, or Firm*—Skjerven, Morrill, MacPherson, Franklin & Friel; Bernard Berman

[57] ABSTRACT

Macro defects in a processed or partly processed semiconductor wafer, liquid crystal display element, disk drive element or the like, are detected using scattered light. By use of automated image processing techniques, a reference image and a sample image are formed from the scattered light and edge enhanced. A difference image is formed by comparing the edge enhanced reference and sample images. The difference image is evaluated using one or more automated image processing techniques such as thresholding, morphological transformations and blob analysis to identify macro defects.

20 Claims, 5 Drawing Sheets

METHOD AND APPARATUS FOR MACRO DEFECT DETECTION USING SCATTERED LIGHT

BACKGROUND

1. Field of the Invention

This invention relates to defect detection using scattered light and more specifically to automatically detecting macro defects on surfaces such as semiconductor wafers, liquid crystal display panels, disk drive platters and the like using scattered light.

2. Description of the Related Art

A well known problem in the semiconductor industry, and other industries where surface defects are a problem, is the need to inspect for macro defects on the active surface e.g. the surface on which circuit elements, electro-magnetic coatings or optical coatings are formed. Typically, these inspections take place numerous times during the fabrication process and can be as often as several times for each fabricated layer. Macro defects can result from scratches and/or particles and typically can range in size from microns ($\mu$m) to a millimeter (mm) or more. Such defects result in a portion of the device being fabricated to function improperly, or not to function at all. Hence, it is important that inspections that can detect macro defects be performed periodically during the fabrication process. In addition, when defects are found it is important to pinpoint the location of each defect to allow that portion of the surface to be indicated as not usable, where possible.

Some prior art relies on manual inspections. Light, typically white light, is directed toward the surface of the substrate from an oblique angle. The presence of a macro defect can cause scattering of the light. An example of such a manual system that is used for visual front and back macro-inspections of semiconductor wafers is the Brightlight 200 manufactured by Irvine Optical Corporation of Burbank, Calif. However, a problem with such prior art systems is that light scattering can result from previous processing, and not indicate a defect. For example, when a semiconductor wafer surface is inspected, the patterns of previous layers created during the fabrication process cause light diffraction; thus an operator is required to distinguish these previous layer signals from a defect. Hence, the ability of that operator to distinguish a macro defect can change as a function of prior layer processing. Thus, manual inspections are subjective and prone to variable results due to fatigue or other factors. In addition, manual inspections are time consuming and often only a portion of the samples are inspected.

Other prior art defect detection systems use an automated image processing and comparison method known as "Golden Template Comparison" (GTC). GTC is described by William M. Silver in *Golden Template Comparison*, Sensors, October 1990, pp. 20–6, which is incorporated by reference herein. Additionally, GTC is available, as a combination of hardware and software, with the Cognex 5600 Vision Processor from Cognex Corp. of Needham, Mass. However, while GTC is a viable method for defect detection in some environments, several problems emerge when GTC is used for inspection of surfaces having complex patterns applied by previous processing using scattered light. For example, GTC can often indicate false defects when sample images contain only minor intensity or color variations. In addition, GTC can also return false defects when star burst patterns caused by diffracted light are present.

Therefore, it would be advantageous to have a method of macro defect detection that does not require a manual inspection or if automated, generate false defect signals. It would also be advantageous to have a method that uses objective criteria for defect detection. Such criteria should not be compromised by false defect detection problems. In addition, it would be advantageous to have a macro defect detection method that can inspect surfaces at a uniformly high throughput rate thus allowing 100% of the samples to be inspected. Finally it would be advantageous to have a macro defect detection system that can be used in a variety of fabrication environments such as semiconductor wafer fabrication, liquid crystal display element fabrication and the like as both a stand alone inspection station or as a portion of some other processing system.

This application is related to previously filed U.S. patent application Ser. No. 08/644,649 filed on May 7, 1996 now U.S. Pat. No. 5,777,792 incorporated herein by reference, and assigned to the assignee of the present invention.

SUMMARY

In accordance with the present invention, macro defects formed on or into the surface of a substrate, such as a semiconductor wafer or liquid crystal display element, are detected using a light scattering technique. The present method and apparatus use an oblique source of incident light and an apparatus to form an image from that light scattered from the surface. ("Light" here is not restricted to the visible spectrum, but refers to electro-magnetic energy that can be scattered.) Using automated image processing techniques, a computer based processing system is first trained using a reference sample, or database of the sample surface to be evaluated, to create an edge enhanced reference template. One or more automated edge enhancement techniques, for example a Sobel edge detector, can be used to form the template.

Once an edge enhanced reference template is created a sample image is acquired and enhanced in the same manner. The resulting enhanced images are compared and a difference image created where edge enhanced scattering effects present in both the template and the enhanced sample image are essentially eliminated. Again, applying one or more automated image processing techniques, for example GTC thresholding, morphological transformations and blob analysis, macro defect detection can be further improved. In this manner, a final image having only macro defects, if any, is produced.

Thus, in accordance with the subject invention, macro inspection of each wafer, for each and every process step, is enabled. Also, by use of the automated image processing taught herein, the uncertainties of manual (human) inspection are avoided, objective macro defect criteria having uniform defect detection thresholds are applied and false defects due to light and color variations and star bursts due to diffraction effects are avoided.

In accordance with the present invention, the detection apparatus can take various forms. In some embodiments a single detector (for instance a charge coupled device video camera) is positioned at a single predetermined angle to detect light scattered from the surface. In other embodiments the detector can be moved to several predetermined positions to enhance inspection of each pattern or of different patterns. In another embodiment, several different detectors are located at different angles to the sample surface or at different positions around the sample to form different images from the light scattered from the various inspection sites to best expose defects. It will be understood, that in all such embodiments of the present invention, the automated image processing can be accomplished using a general purpose computer with appropriate program routines or by using a specialized image processing system with other appropriate program routines. Finally, in some embodiments of the present invention, inspection is carried out by a stand alone inspection system while other embodiments this apparatus may be incorporated into other suitable processing equipment if so desired.

BRIEF DESCRIPTION OF THE DRAWINGS

The present invention may be better understood, and its numerous objects, features, and advantages made apparent to those skilled in the art by referencing the accompanying drawings. For ease of understanding and simplicity, common numbering of elements within the illustrations is employed where the element is the same is between illustrations.

DETAILED DESCRIPTION

Embodiments of the present invention will be described with reference to the aforementioned figures. These drawings are simplified for ease of understanding and description of embodiments of the present invention only. Various modifications or adaptations of specific methods and or structures may become apparent to those skilled in the art as embodiments of the present invention are described. All such modifications, adaptations or variations that rely upon the teachings of the present invention, and through which these teachings have advanced the art, are considered to be within the spirit and scope of the present invention. For example, in some embodiments of the present invention a sample is evaluated using a reference template formed from one or more known-good reference samples, while in other embodiments the reference template is formed from a database of the sample area. Typically, known-good reference samples are determined by manually inspecting a group of potential reference samples and selecting those of the highest quality.

Figure 1:
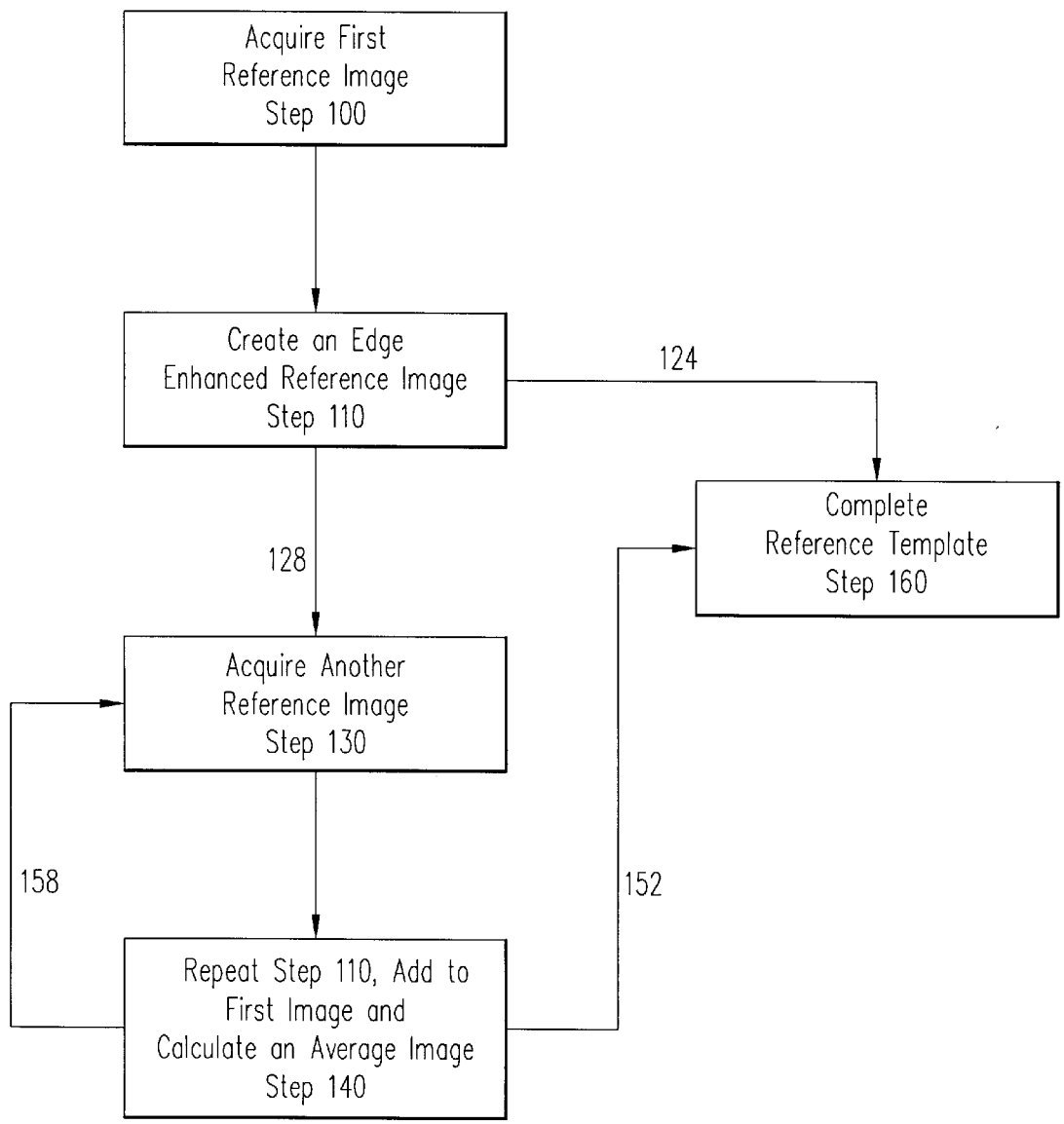
FIG. 1 is a block diagram of process steps used to form a reference image using an embodiment of the present invention.

Turning to FIG. 1, a block diagram of the process steps used in the training phase of an embodiment of the present invention is shown ("Training" refers to the well known step in image analysis of providing a nominal "correct" image to which a sample to be inspected is later compared). Step 100 provides for acquiring a first reference image. Once acquired, the first reference image is edge enhanced to form a first edge enhanced reference image, Step 110, and stored. While a number of automated image processing edge enhancement techniques are known, for example, Difference, Roberts and Laplace, among others, a Sobel edge detector has been found desirable. However, any of the other techniques mentioned can be employed. If only a single reference image is used to form the edge enhanced reference image, for example where the image acquisition of Step 100 is from a database of the sample area, then branch 124 is selected and the image of Step 110 is used as the reference template of is Step 160. As known, advanced pattern forming methods often involve generating patterns from a digital representation of the pattern, commonly referred to as a pattern database. Thus some embodiments of the present invention can use these databases for forming the image produced by Step 100.

Alternatively, if additional training is desired to account for acceptable process variations, branch 128 is followed and another reference image, Step 130, acquired. This subsequent image is edge enhanced and the result added toced to the first edge enhanced reference image to form an average image, Step 140. If no additional training is desired, branch 152 is followed and the image of Step 140 becomes the reference template of Step 160. However, where additional training is desired, branch 158 is selected and Steps 130 and 140 repeated until the training phase is completed and a reference template 160 formed. It is common, even among substrates of the highest quality, for process variations to occur. Hence training using multiple know-good reference samples is employed to take these variations into consideration thus reducing the possible number of false defect signals. In addition, use of a database to form a reference image can be combined with a single known-good reference sample or multiple known-good reference samples to form reference template 160 as described above.

In some embodiments, more than one reference template 160 will be formed where each template 160 is based upon different lighting or imaging angles. Such multiple reference templates 160 allow for multiple inspections where different lighting and or imaging angles can improve macro defect detection.

Figure 2:
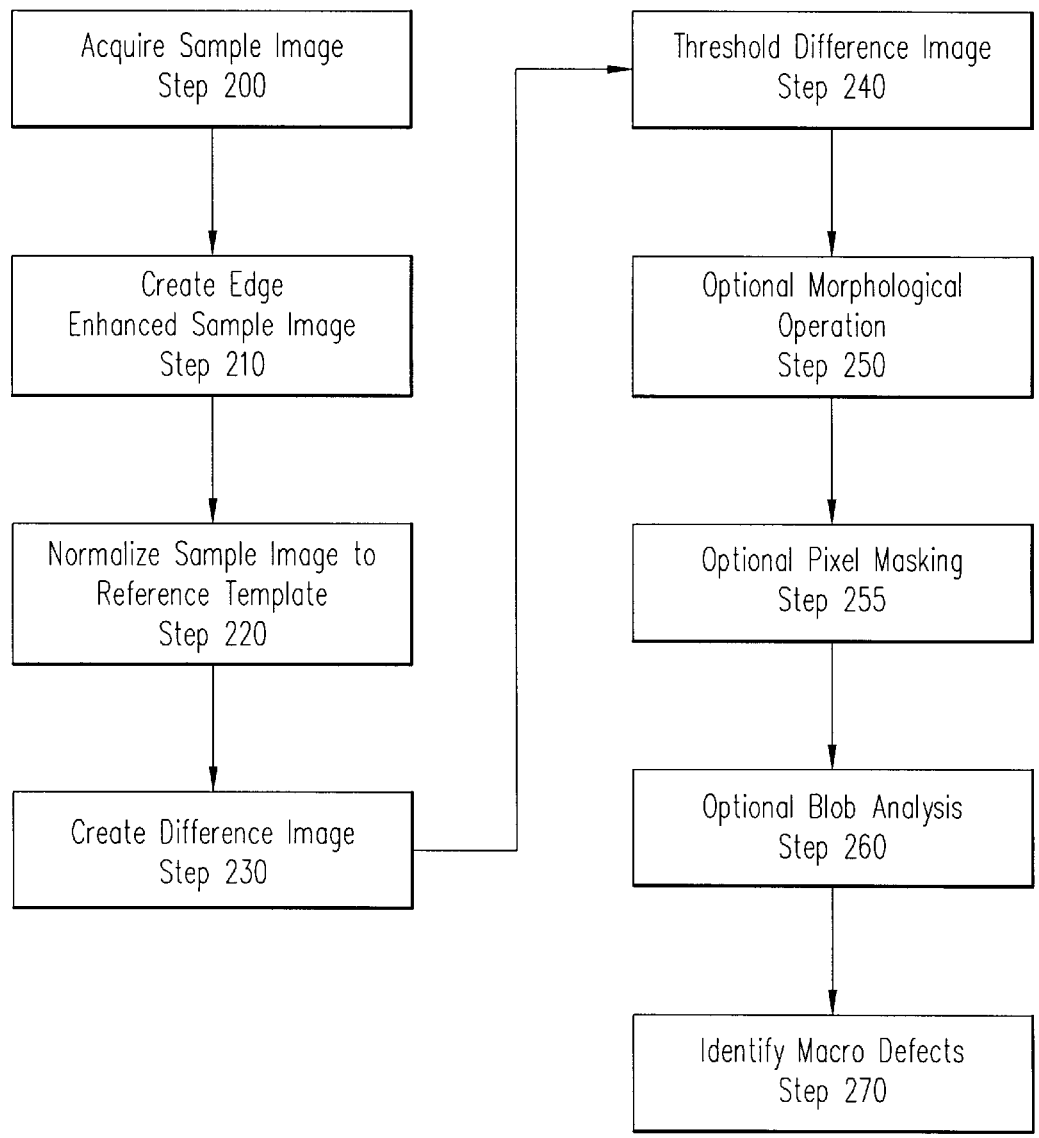
FIG. 2 is a block diagram of process steps used to form and evaluate a sample image using an embodiment of the present invention.

Upon completion of the training phase of FIG. 1, automated inspection can commence. Referring now to FIG. 2, a block diagram of the process steps used in the detection phase of an embodiment of the present invention is shown.

In Step 200, a sample image is acquired using the same lighting and imaging angle employed to acquire the reference image of Step 100. An edge enhanced image of sample image 200 is created in Step 210 using the same edge enhancement technique employed in the formation of reference template 160. Edge enhanced image 210 is then normalized to reference template 160. Any of the known normalization techniques such as Identity Transformation, Tails Matching, Histogram Matching or Mean and Standard Deviation can be employed and all compensate for changes in lighting and aperture between training and detection phases.

Once normalization is complete, a difference image is created in Step 230. This difference image will contain elements of reference template 160 missing from image 210 as well as extra elements found in image 210. It will be understood however, that unlike GTC, the difference image of the present invention is based on the difference between two edge enhanced images. Edge enhanced images are typically pixelized representations of a real image where only edges have significant gray scale values. Thus, as essentially only edges are represented, image variations due to light or color differences or random diffraction effects are eliminated as the gradient for these changes are too small to give rise to edges when edge detection is applied. In addition, automated processing to form the difference image requires less processing resource when compared to image subtraction as employed in GTC.

After difference image 230 is formed, a threshold process is employed to form thresholded difference image 240. A specific threshold method is selected and the pre-selected method employed to examine each pixel in difference image 230 and move a binarized representation of that pixel to image 240. Thus once formed, thresholded difference image 240 is essentially an array of pixels where macro defects are represented as pixels, or contiguous groups of pixels, having a gray scale value in excess of a value determined by the threshold method selected. Thus macro defect identification 270 can be performed without optional Steps 250, 255 and 260. A variety of threshold methods can be employed. In some embodiments, the threshold method selected can use a uniform value for each pixel of an image, while in other embodiments a set of threshold values can be used where one or more values of the set of values can be applied to each pixel.

Optional Steps 250, 255 and 260 provide for enhancements of image 240 and can allow for accurate macro defect detection. The morphological operation of optional Step 250 filters image 240 to eliminate clusters (contiguous groups) of pixels that do not represent true macro defects, while leaving intact those that do. Typically, morphological filtering is based upon a morphological filtering element (not shown) where all clusters, or groups of pixels, in image 240 having a size that does not exceed the size of the element selected are filtered out. Thus if an element having a size of 2 pixels by 3 pixels is selected, then an image 250 is created from image 240 where all elements less than the size of the element are not represented.

Optional Step 255 involves defining a masking image that defines pixels that should not be considered, or "masked" when detecting macro defects. Examples of pixels that can be advantageously "masked" are those pertaining to repetitive features, pixels identified from a previous inspection as having a defect or the like. In this manner, finding a defect identified at a previous inspection or misclassification of a repetitive feature as a defect can be prevented.

When pixels are "masked" in accordance with optional Step 255, they are suppressed to zero or some other predetermined value. For example, where a pixel of Thresholded Difference Image 240*a* (FIG. 3) is "masked" the value applied will be less that any threshold value applied to that pixel used to form image 240*a*. Thus if a pattern related pixel 294 (FIG. 3) is "masked", it will be removed from image 240*a* and thus any further consideration as a potential defect. Pixels "masked" in the manner of optional Step 255 can be processed as a portion of Steps 230, 240 or 250 or as a stand alone step (as indicated) after Step 230 but before Step 270.

The blob analysis of optional Step 260 is a process that identifies groups of pixels or blobs (not shown) and calculates each blob's dimensions, area and center of mass. In addition the analysis can assign an identifying flag to each blob. The analysis can be either direct or differential. A direct blob analysis is performed using the difference image of Step 230 to create an blob error image 260. A differential analysis uses both difference image 230 and the threshold difference image of Step 240 to calculate blob error image 260. In either case, the output of the analysis is a total count of defect pixels in addition to the aforementioned calculations for each blob. Based upon the blob analysis results, further discrimination rules can be derived to correctly identify defects. For example, if a blob does not exceed a certain size, then it is not considered a defect; or if the elongation does not indicate that it is a scratch, then it is ignored.

Figure 3:
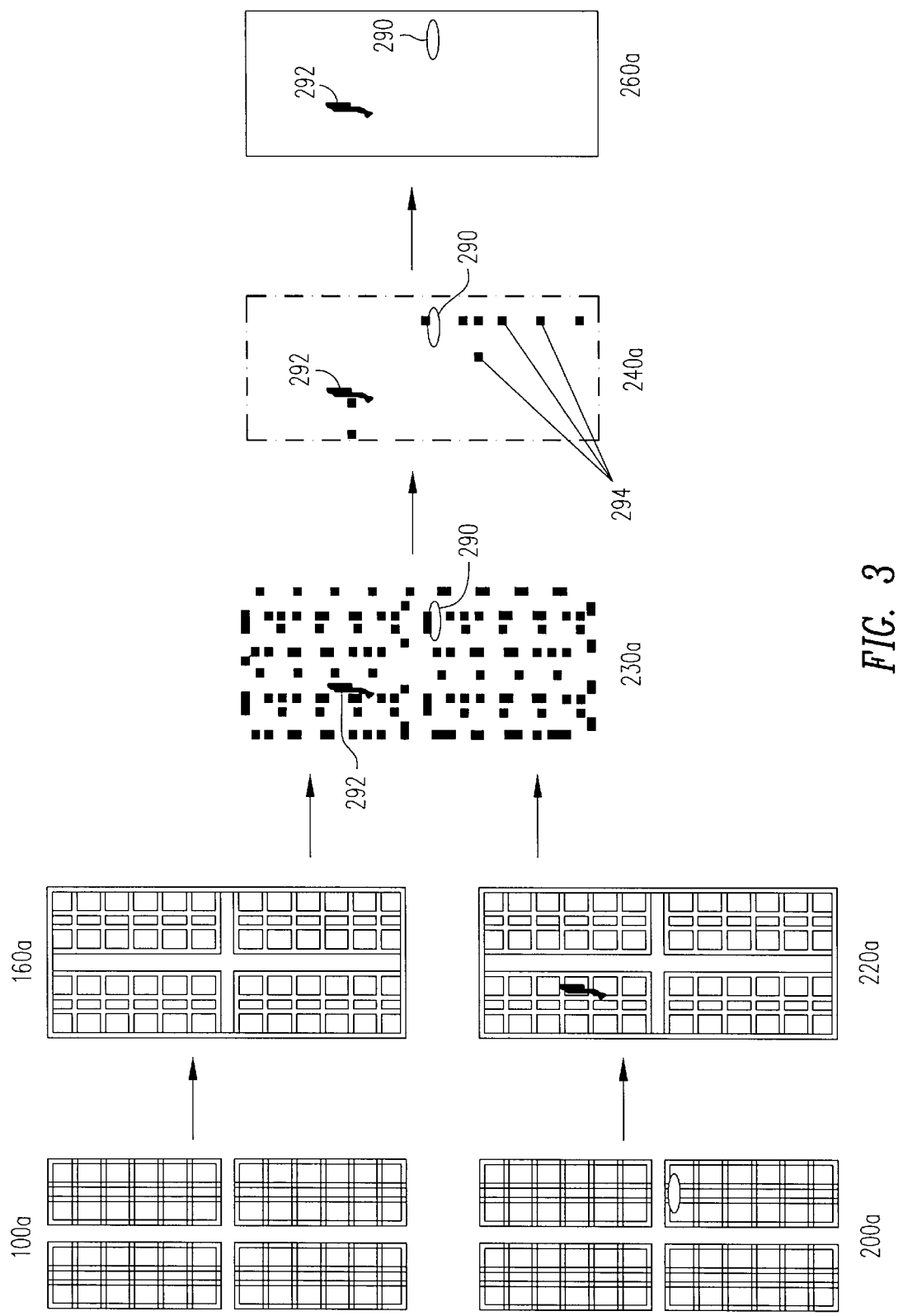
FIG. 3 is simplified representation of images from a macro defect inspection in the manner of an embodiment of the present invention.

Referring now to FIG. 3, a simplified representation of images from a macro defect inspection in the manner of an embodiment of the present invention is illustrated. Following the steps of FIG. 1, one or more known-good reference images 100*a* are acquired and transformed into edge enhanced reference template 160*a*. Sample image 200*a*, having macro defects 290 and 292, is acquired and transformed into the normalized, edge enhanced image 220*a* of Step 220 (FIG. 2). Then, as described previously, the images are aligned and an image subtraction is performed to create difference image 230*a*. As depicted, the number of pattern related pixels remaining in image 230*a* is less than in either image 200*a* or 220*a*, making defects 290 and 292 more visible in image 230*a*. However, after the thresholding of Step 240 (FIG. 2), the number of pattern related pixels 294 is reduced further and an image 240*a* is created where defects 290 and 292 are easily identifiable. Where desired, an optional blob analysis, as per Step 260 (FIG. 2), can be performed and as indicated in image 260*a* enhance the detection of macro defects 290 and 292 further.

The above described embodiments of a method for automated macro defect detection can be accomplished using a combination of computer hardware (circuitry) and software. The computer hardware is either a general purpose computer or circuitry specifically designed for image processing and the software is created to perform the operations described using the hardware selected. In light of this disclosure, coding such software would be well within the skill of one of ordinary skill in the art. In this manner, the criteria for any inspection is predetermined for the actual inspection process employed and the computer hardware/software combination insures that these embodiments provide for an objective inspection process. In addition, it has been found that embodiments of present invention can perform all image processing operations in less than 15 seconds for each substrate thus providing a high throughput that makes possible 100% inspection.

Figure 4:
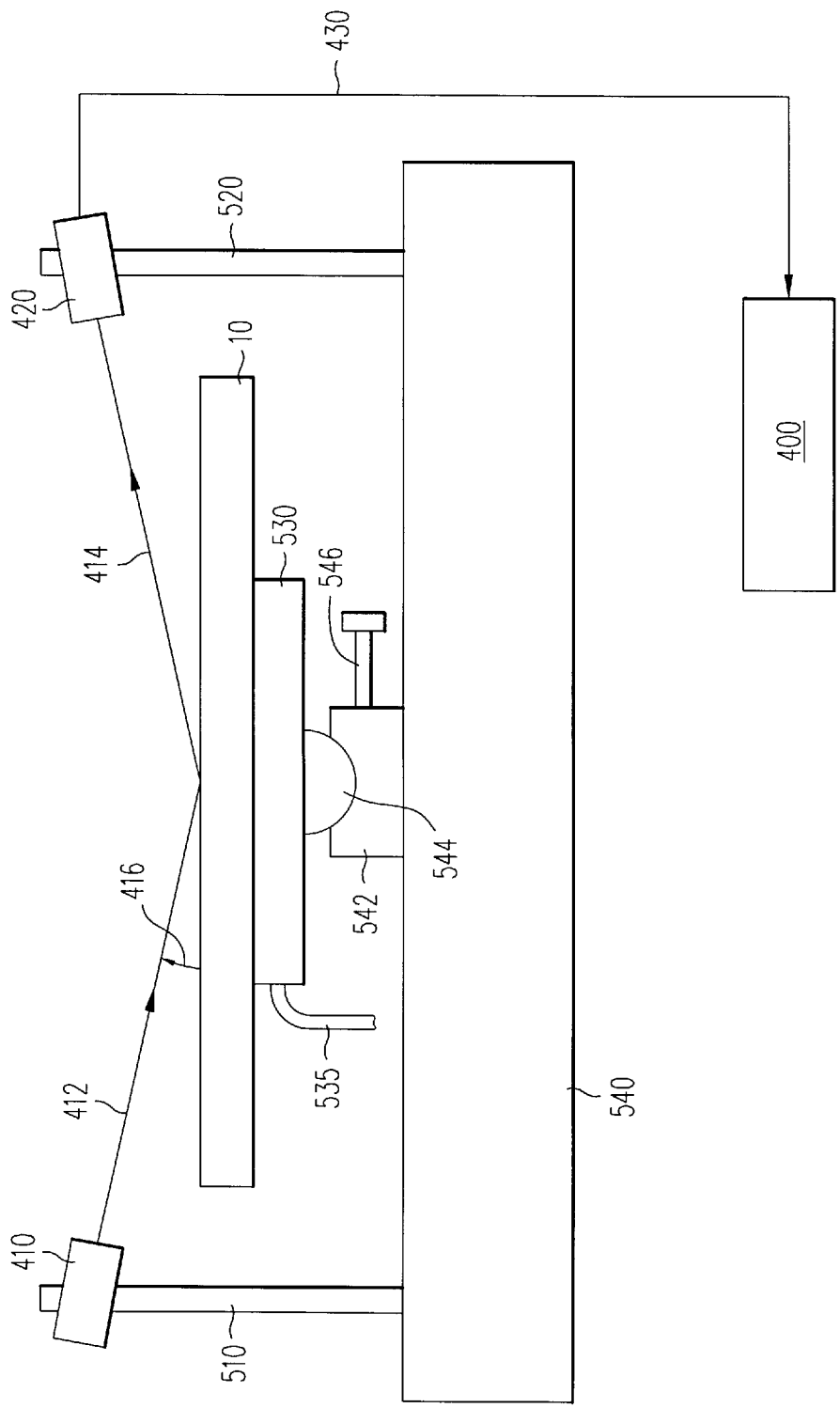
FIG. 4 shows a diagrammatically a semiconductor wafer inspection station having a single detector camera and a single oblique light source.

An embodiment of an inspection apparatus in accordance with this invention is shown schematically in FIG. 4. While only a single camera or detector 420 and single light source 410 is shown, other embodiments having multiple detectors 420 and light sources 410 are within the scope and spirit of the present invention. For example, in one embodiment of this apparatus as shown in more detail in FIG. 5, four light sources 410 and detectors 420 are used. Returning to FIG. 4, both light source 410 and detector 420 are coupled to support members (not shown) such that each can be adjusted to optimize macro defect detection using scattered light for each sample, for example by modifying a grazing or oblique angle 416, less than 45°, of a light beam 412 that is incident to the wafer 10 surface. In addition, the coupling of camera 420 allows positioning at appropriate meridional and azimuthal angles for sensing forward scattered light 414. By optimizing the three angles, signal to background and signal to noise ratios of the camera 420 are optimized. The specific method of this coupling and means through which adjustment is provided are not critical to embodiments of the present invention, and any such coupling is thus within the present invention's spirit and scope.

FIG. 4 also illustrates a base plate 540 having an X–Y motion device 542 equipped with a rotational motion device 544 fixably coupled thereto. A substrate holder 530 is fixed to rotational motion device 544 such that a full range of X–Y and rotational movement of a substrate 10, detachably coupled to holder 530, is provided. In this manner, when an inspection area 15 (FIG. 5) is less than all of substrate 10, or when image alignment and registration is required, substrate 10 can be moved to complete the inspection.

Device 400 is shown coupled to detector 420 by and through data coupling 430. In combination, device 400 and detector 420 provide for performing the steps of FIGS. 1 and 2. Thus detector 420 and device 400 can vary in their functionality for different embodiments of the present invention. For example, in some embodiments detector 420 can be an analog video camera providing an analog signal through coupling 430. Device 400 can then provide for analog to digital conversion of the signal and perform all image processing, memory and defect detection functions. In other embodiments, detector 420 can be CCD (Charge Coupled Device) cameras providing a digital signal thus removing the requirement of analog to digital conversion from device 400.

It will also be understood that in some embodiments, device 400 can be a general purpose computer having software programs resident therein for performing the steps of FIGS. 1 and 2. In other embodiments, device 400 can be a highly specialized video processor, such as a Cognex 5600 video processor, having software programs resident therein for performing the steps of FIGS. 1 and 2.

Figure 5:
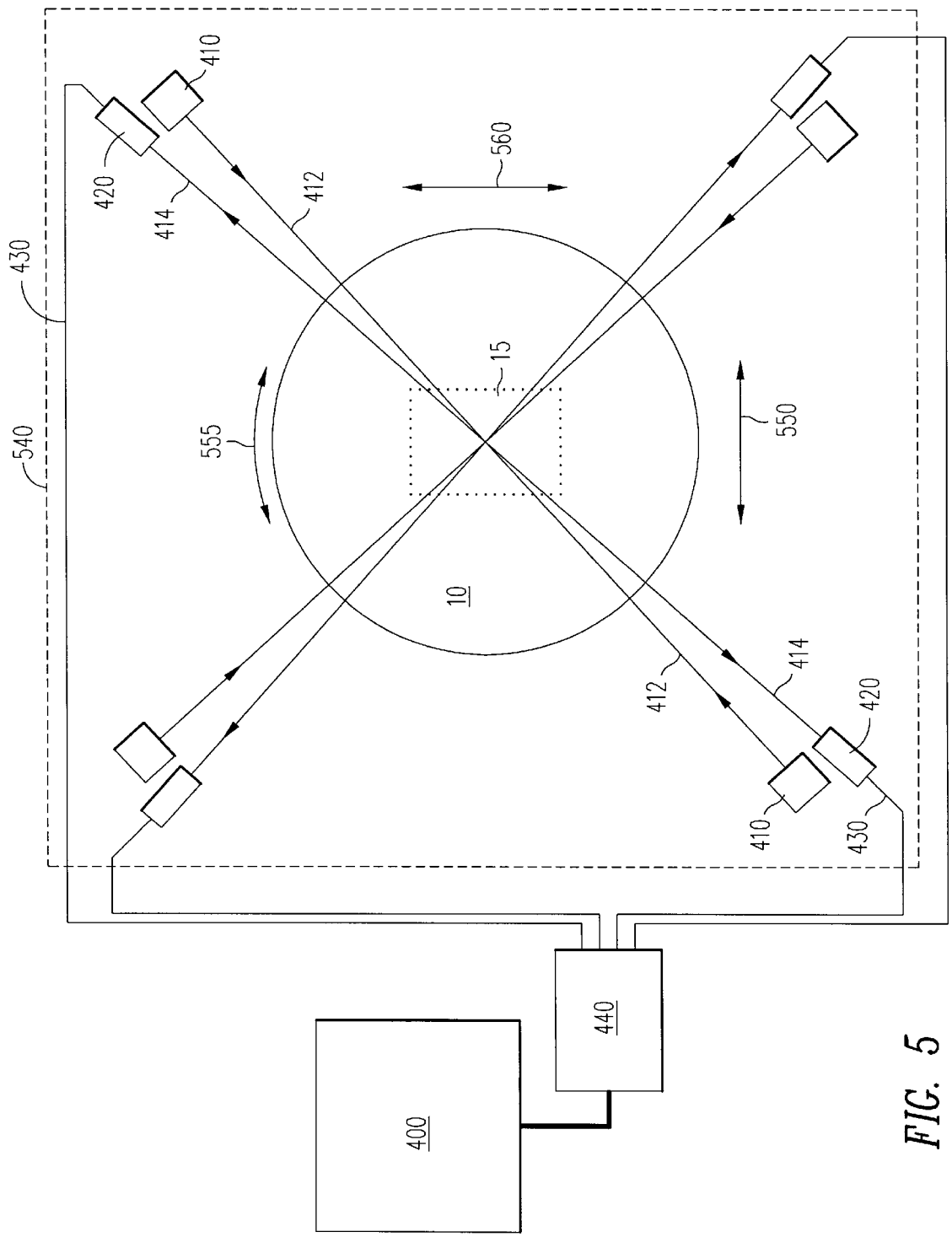
FIG. 5 shows is a plan view of an apparatus similar to that of FIG. 4, but having multiple detector cameras and multiple oblique light sources.

Turning now to FIG. 5, a plan view of an apparatus similar to that of FIG. 4, but having four detectors or cameras and four light sources is depicted. It will be understood that the specific number and arrangement of detectors 420 and light sources 410 are illustrative only, and that other numbers and arrangements possible. In addition, as mentioned with respect to FIG. 4, each detector 420 and light source 410 is coupled to base plate 540 such that the defect detection can be optimized. It will also be understood that devices for providing X-motion 550 and Y-motion 560, as well as rotation 555 are provided but not shown.

As FIG. 5 depicts multiple cameras or detectors 420, a video signal multiplexer 440 is required to couple signals from detectors 420 through data coupling 430 to device 400. In some embodiments of the present invention, multiple detectors 420 are used to acquire images sequentially, thus multiplexer 440 functions as a switching device providing the proper signal to device 400 at the proper time. In other embodiments, image acquisition can be performed using multiple images from more than one detector 420. Thus multiplexer 440 can function as an image processor to provide an appropriate signal to device 400.

Thus embodiments of the present invention have been described that provide an apparatus for performing the steps of FIGS. 1 and 2. One of ordinary skill in the art will realize that while the embodiments shown illustrate specific combinations of light sources 410, cameras 420, signal multiplexer 440 and computational device 400, other combinations are possible that are within the spirit and scope of the present invention.

It will also be realized that the embodiments of the present invention described can be stand-alone systems or be incorporated within other processing equipment. For example, a macro defect detection system in accord with the present invention can be advantageously incorporated within a photolithography tool to detect the presence of a photoresist coating prior to exposure.

Finally, it will be realized that embodiments of the present invention described herein enable an automated macro defect detection method and apparatus therefor. In addition, it will be realized that the methods and apparatus described eliminate the uncertainties and subjectivity of manual (human) inspection for macro defects by using various automated image processing steps that advantageously reduce or eliminate false defect detection of the prior art GTC method due to light and color variations and diffraction effects.

We claim:

1. A method for detecting macro defects on a sample surface comprising the steps of:

forming a first edge enhanced image of a reference;

directing light from a light source onto said sample surface at an oblique angle wherein said sample surface corresponds to said reference;

detecting light from said light source scattered by said sample surface;

forming a test image of said sample surface from the scattered light;

performing an edge enhancement of said image to form a second edge enhanced image;

forming a difference image by subtracting said first edge enhanced image from said second enhanced image;

forming a thresholded difference image by applying a pre-selected threshold method to said difference image, wherein said thresholded difference image further comprises an array of pixels; and determining a presence or absence of macro defects wherein each pixel or contiguous group of pixels, of said thresholded difference image having a gray scale value in excess of a value determined by said threshold method is defined as a macro defect.

2. The method of claim 1, wherein said reference comprises a regular pattern of light scattering features on a reference surface that represent a desired pattern.

3. The method of claim 2, wherein said first edge enhanced image is formed from an image of said reference surface.

4. The method of claim 2, wherein forming said first edge enhanced image comprises the steps of:

directing light from said light source onto said reference surface at said oblique angle;

detecting light from said light source scattered by said reference surface;

forming an image of said reference surface from the scattered light; and performing an edge enhancement of said image.

5. The method of claim 4, wherein forming said image of said reference surface comprises forming a plurality of temporary images, each temporary image formed of a different reference surface, and averaging said plurality of temporary images.

6. The method of claim 4, wherein forming said image of said reference surface comprises the steps of:

forming one or more first temporary images, each first temporary image formed of a different reference surface;

forming a second temporary image, wherein said second temporary image is formed of a database representation of said reference surface; and averaging said one or more first temporary images and said second temporary image.

7. The method of claim 1, wherein said reference is a database representation of a regular pattern of light scattering features that represent a desired pattern.

8. The method of claim 1 wherein forming a difference image comprises normalizing said second edge enhanced image to said first edge enhanced image.

9. The method of claim 1 wherein determining a presence or absence of macro defects further comprises performing a morphological operation of said thresholded difference image.

10. The method of claim 1 wherein determining a presence or absence of macro defects further comprises performing a direct or differential blob analysis.

11. A method of scattered light macro defect detection comprising the steps of:
   training a macro defect detection apparatus, wherein said training comprises forming a reference template image;
   acquiring a sample image of a sample surface from scattered light with a camera;
   forming an edge enhanced image of said sample image;
   normalizing said edge enhanced image to said reference template image;
   forming a difference image of said normalized edge enhanced image and said reference template;
   forming a thresholded difference image of said difference image;
   performing a direct blob analysis of said thresholded difference image or a differential blob analysis of said difference image and said thresholded difference image; and
   determining a presence or absence of macro defects using said direct or differential Blob analysis and thresholded difference image;
   wherein forming said edge enhanced image, normalizing said edge enhanced image, forming said difference image, forming said thresholded difference image, performing said direct or differential blob analysis and said determining a presence or absence of macro defects is performed by said macro defect detection apparatus.

12. The method of claim 11, wherein forming said reference template image comprises forming an edge enhanced image of a reference surface.

13. The method of claim 12, wherein forming said edge enhanced image comprises substituting a database representation of a regular pattern of light scattering features that are not macro defects for said reference surface.

14. The method of claim 12, wherein forming said edge enhanced image comprises the steps of:
   forming a plurality of temporary images wherein each temporary image is formed of a different reference surface; and
   forming an average image of the plurality of temporary images, wherein said edge enhanced image is formed of said average image.

15. The method of claim 11, wherein acquiring a sample image of a sample surface comprises illuminating said sample surface with a light source positioned at an oblique angle to said sample surface.

16. An apparatus to inspect for macro defects on a substrate comprising:
   a support for holding said substrate;
   a light source for directing light onto a surface of said substrate when said substrate is on said support;
   a detector located to receive light scattered from said surface of said substrate; and
   an automated processor coupled to said detector for comparing an edge enhanced image of said surface to an edge enhanced reference template, thereby to determine a presence or absence of macro defects on the surface of the substrate.

17. The apparatus of claim 16, further comprising at least one additional detector located to receive scattered light from the surface of the substrate, the additional detector being located to detect scattered light at a different angle than is the first detector.

18. The apparatus of claim 16, further comprising a mechanism coupled to the substrate for moving the substrate relative to the detector.

19. The apparatus of claim 18, wherein the support includes means for rotating the substrate in a plane defined by its surface.

20. The apparatus of claim 16, wherein the detector comprises a charged coupled device camera.

* * * * *

UNITED STATES PATENT AND TRADEMARK OFFICE
CERTIFICATE OF CORRECTION

PATENT NO. : 5,859,698
DATED : January 12, 1999
INVENTOR(S) : Henry K. Chau et al.

Page 1 of 2

It is certified that error appears in the above-identified patent and that said Letters Patent is hereby corrected as shown below:

Col. 2, line 16, delete "U.S. Patent No. 5, 777,792"; add --U.S. Patent No. 5,777,729--

Col. 3, line 17, delete "is" after "same";

Col. 8, line 29, delete all through Col. 8, line 60 and substitute:

--3. The method of Claim 1, wherein said reference is a database representation of a regular pattern of light scattering features that represent a desired pattern.

4. The method of Claim 2, wherein said first edge enhanced image is formed from an image of said reference surface.

5. The method of Claim 2, wherein forming said first edge enhanced image comprises the steps of:
 directing light from said light source onto said reference surface at said oblique angle;
 detecting light from said light source scattered by said reference surface;
 forming an image of said reference surface from the scattered light; and
 performing an edge enhancement of said image.

6. The method of Claim 5, wherein forming said image of said reference surface comprises forming a plurality of temporary images, each temporary image formed of a different reference surface, and averaging said plurality of temporary images.

UNITED STATES PATENT AND TRADEMARK OFFICE
CERTIFICATE OF CORRECTION

PATENT NO. : 5,859,698
DATED : January 12, 1999
INVENTOR(S) : Henry K. Chau et al.

It is certified that error appears in the above-identified patent and that said Letters Patent is hereby corrected as shown below:

7.    The method of Claim 5, wherein forming said image of said reference surface comprises the steps of:

forming one or more first temporary images, each first temporary image formed of a different reference surface;

forming a second temporary image, wherein said second temporary image is formed of a database representation of said reference surface; and averaging said one or more first temporary images and said second temporary image.--

Signed and Sealed this

Thirtieth Day of January, 2001

Attest:

Q. TODD DICKINSON

*Attesting Officer*    *Director of Patents and Trademarks*